(12) United States Patent
Harms et al.

(10) Patent No.: US 9,795,469 B2
(45) Date of Patent: Oct. 24, 2017

(54) SURGICAL IMPLANT

(71) Applicant: Johnson & Johnson Medical GmbH, Somerville, NJ (US)

(72) Inventors: Volker Harms, Hamburg (DE); Susan Cooper, Hamburg (DE); Dajana Kaiser, Hamburg (DE); Christoph Walther, Kattendorf (DE)

(73) Assignee: Johnson & Johnson Medical GMBH, Norderstedt (DE)

( * ) Notice: Subject to any disclaimer, the term of this patent is extended or adjusted under 35 U.S.C. 154(b) by 170 days.

(21) Appl. No.: 14/206,005

(22) Filed: Mar. 12, 2014

(65) Prior Publication Data
US 2014/0276999 A1    Sep. 18, 2014

(51) Int. Cl.
*A61B 17/04*    (2006.01)
*A61F 2/00*    (2006.01)

(52) U.S. Cl.
CPC .... *A61F 2/0063* (2013.01); *A61F 2002/0068* (2013.01)

(58) Field of Classification Search
CPC ............ A61F 2/0063; A61F 2002/0068; A61F 2002/0072
See application file for complete search history.

(56) References Cited

U.S. PATENT DOCUMENTS

| | | | | |
|---|---|---|---|---|
| 3,190,289 A * | 6/1965 | Patience | .................. | A61F 13/36 604/362 |
| 6,645,597 B1 * | 11/2003 | Swain | .................. | A01K 1/0107 428/68 |
| 2002/0013590 A1 * | 1/2002 | Therin | .................. | A61F 2/0063 606/151 |
| 2004/0019360 A1 * | 1/2004 | Farnsworth | ........... | A61F 2/0063 606/151 |
| 2005/0192600 A1 * | 9/2005 | Nicolo et al. | .................. | 606/151 |
| 2008/0147099 A1 | 6/2008 | Uen | | |
| 2009/0069826 A1 * | 3/2009 | Walther et al. | ............... | 606/151 |
| 2009/0149875 A1 * | 6/2009 | Abele | .................. | A61F 2/0063 606/151 |
| 2011/0118851 A1 | 5/2011 | Eldridge et al. | | |
| 2011/0152897 A1 * | 6/2011 | Bates | ............... | A61B 17/00234 606/151 |

FOREIGN PATENT DOCUMENTS

| | | |
|---|---|---|
| EP | 2032073 | 8/2012 |
| WO | WO 03/037215 | 5/2003 |
| WO | WO 2011/159700 | 12/2011 |

\* cited by examiner

*Primary Examiner* — Richard Louis
(74) *Attorney, Agent, or Firm* — E. Richard Skula (57) ABSTRACT

A surgical implant (100) comprises a mesh-like, flexible basic structure (104) having a center area and an outer periphery (120), wherein the outer periphery (120) has a polygonal shape with N corners (122), N being at least 3. The implant (100) may comprise at least two pockets (124), each pocket (124) extending from a peripheral line which connects two corners (122) of the outer periphery (120) of the basic structure (104) towards the center area of the basic structure (104). The center area of the basic structure (104) can be marked by a center marking (130), wherein directional indicators (132) point from the center marking (130) to at least two corners (122) of the outer periphery (120) of the basic structure (104).

14 Claims, 6 Drawing Sheets

SURGICAL IMPLANT

CROSS REFERENCE TO RELATED APPLICATIONS

This application claims priority from German Patent Application DE 102013004486.3 filed Mar. 14, 2013 the disclosure of which is hereby incorporated by reference in its entirety.

FIELD OF THE INVENTION

The invention relates to a surgical implant, in particular to a surgical implant having an areal basic shape and comprising a mesh-like, flexible basic structure. The implant can be applied, e.g., as a ventral hernia device in the intraperitoneal space, but may be useful also for other indications of ventral hernia defects (like umbilical hernia defects, incisional hernia defects), for hernia prevention and for repairing a tissue or muscle wall defect in general.

BACKGROUND OF THE INVENTION

EP 2 032 073 A discloses an implantable medical device comprising a tissue repair material having two sides (faces) and an outer perimeter (periphery) with at least one side adapted for ingrowth of cells. A cuff is formed from the outer perimeter to overlap onto a side of the tissue repair material, creating an opening between the cuff and the tissue repair material. The cuff forms a fixation area at the outer edge of the device for use in joining the device to tissues of a patient.

US 2008/0147099 A shows a bi-layer patch device for hernia repair including a first layer and a second layer. The first layer is cut to form locating flakes. The edges of the first layer and the second layer are connected to form a pocket. The second layer further comprises an auxiliary layer. The patch can be attached to a cavity of the peritoneum for repairing a hernia.

US 2011/0118851 A discloses an implantable prosthesis for repairing or augmenting anatomical weaknesses or defects, and is particularly suitable for the repair of soft tissue and muscle wall openings. The prosthesis includes a repair fabric that is constructed and arranged to allow tissue ingrowth and is susceptible to erosion and the formation of adhesions with tissue and organs. One or more regions of the prosthesis may be configured to inhibit erosion and/or the formation of adhesions. The prosthesis may include an erosion-resistant edge, which can be provided along an opening that is adapted to receive a tube-like structure, such as the esophagus.

Pocket-shaped implants which are currently available on the market show some disadvantages. The pockets are formed by placing various material layers on top of each other, followed by, for example, a seam connection at the edges. Sometimes, support rings are included as well in the edge areas. Implant fixation is only permitted inside these edge connections. This leads to non-fixated edge material which may result in bulged and/or folded edge areas. Furthermore, stiff materials, for example support rings, tend to fail (by bending or breaking). Problems concerning tissue ingrowth as well as organ irritations or injuries can result from the above-mentioned disadvantages. As a consequence of the assembling process (positioning of different material layers on top of each other), the outer edges of some pocket-shaped implants are not covered with anti-adhesive materials and pose a potential risk for adhesions.

Nowadays, the fixation of such pocket-shaped implants is often performed with staplers or tackers. Due to the shape of the current open IPOM (Intra-Peritoneal Onlay-Mesh technique) devices (oval, circular or rectangular with significantly rounded edges), predefined positions of the first fixation points cannot be found.

Furthermore, a correct placement in terms of orientation and centering of the implant after insertion into the abdominal cavity is often difficult.

WO 2011/159700 A describes a composite implant which can be used for repairing hernias, especially incisional hernias, particularly for intraperitoneal applications. This implant includes an alignment marker, which is asymmetric and Is adapted to show the center of the implant and the preferred placement direction for the implant.

WO 2003/037215 A discloses an areal implant having a mesh-like basic structure and a marking in a central region that indicates the center of the implant. A marking line runs through the central marking. The central marking and the marking line can be used for aligning the implant over a surgical opening for reinforcing the tissue.

These implants may give an indication on the orientation of the implant. However, they do not clearly inform the surgeon on the actual position of the periphery of the implant, which might be concealed by bodily tissue. Such information is important because, generally, the implant is fixed to bodily tissue in its peripheral area.

BRIEF SUMMARY OF THE INVENTION

The object of the invention is to provide a surgical implant, in particular useful for hernia repair, which can be easily handled and which facilitates the surgical procedure.

This object is achieved by a surgical implant having the features of claim 1. Advantageous versions of the invention follow from the dependent claims.

The surgical implant according to the invention comprises a mesh-like, flexible basic structure having a center area and an outer periphery. The outer periphery comprises a polygonal shape having N corners, wherein N is at least 3. The term "corner" also includes somewhat rounded forms. Preferably, the surgical implant has a hexagonal or an octagonal shape, i.e. N=6 or N=8

A polygonally shaped implant has a generally well-defined and compact form, which assists the surgeon in estimating the boundaries of the implant, which often is not straightforward because part of the implant may be hidden by bodily tissue.

In advantageous embodiments according to a main aspect of the invention, the surgical implant comprises at least two pockets, wherein each pocket (or pouch) extends from a peripheral line or edge line (which connects two corners of the outer periphery of the basic structure) towards the center area of the basic structure. Preferably, the implant comprises N pockets.

The pockets might be separately manufactured and attached to the basic structure. In advantageous embodiments, however, the mesh-like basic structure and the pockets are folded about fold lines from a common blank, wherein the fold lines are located at the outer periphery of the basic structure. The pockets are accessible via respective edges opposite to the fold lines. In this terminology, the common blank is made of mesh-like material and comprises the material of the basic structure plus the material of the pocket flaps folded back towards the basic structure along the fold lines; and one face of a pocket is formed from the pocket flap, whereas the opposite face of the pocket is part of the basic structure.

When the surgical implant according to the invention is used, e.g., for hernia repair, the face including the pocket flaps (parietal side, fixation layer) is pointing to the surgeon, whereas the opposite face (visceral side, repair layer) of the implant is facing the patient's interior.

In advantageous embodiments of the invention, material of a given pocket overlaps with material of an adjacent pocket in a respective overlap area, wherein in the overlap area material of the adjacent pockets is connected to each other. The overlap areas can be design, e.g., strip-like, curved, zigzag-shaped, asymmetric or diamond-shaped. In the overlap areas, the material of adjacent pockets can be connected, e.g. by welding, gluing or sewing. A material used for gluing (e.g. a film material) or sewing (e.g. a thread material) can be permanent (non-absorbable), absorbable (resorbable) or partially absorbable.

The material of a pocket flap can also be connected to the basic structure outside of an overlap area. This may be advantageous if the edge of the pocket flap, via which the pocket is accessible, is relatively long, because it stabilizes the pocket when used for fixing the implant to bodily tissue. For example, this connection can be point-like, and it is advantageous when a directional indicator (see below) aims at such point-like connection area.

On the other hand, it is also conceivable that adjacent pockets are not attached to each other in the overlap areas or even that the pocket flaps are formed in a way that there is no overlap between adjacent pockets. In such cases, the shape of the pockets may nevertheless be rigid enough to enable the function of a fixation layer for the implant.

In advantageous embodiments of the invention, an anti-adhesive film (or, more general, anti-adhesive layer) is located at the face of the basic structure facing away from the pockets, i.e. on the visceral side of the implant. The anti-adhesive layer resists and prevents ingrowth of bodily tissue into the mesh-like basic structure and acts anti-adhesive. Preferably the anti-adhesive film/layer is absorbable so that it exhibits its effect during the initial healing period, when this is important. The anti-adhesive film/layer may cover the area of the basic structure and also extend beyond the outer periphery of the basic structure where the anti-adhesive film/layer is folded back together with the material (flaps) of the pockets. Preferably, less than 50% of the area of the pocket flap material is covered by the anti-adhesive layer. In this way, the edges of the surgical implant are also protected from generally undesired adhesion to bodily tissue.

Suitable materials for the anti-adhesive film/layer are, e.g. poly-p-dioxanone (PDS), ϵ-caprolactone, copolymers of glycolide and ϵ-caprolactone (e.g. MONOCRYL™ film of Ethicon), oxygenized regenerated cellulose (ORC), collagens or combinations thereof, but other anti-adhesive and bio-compatible materials known in the art can be considered as well. The anti-adhesive film can have any thickness in the range of, e.g., 2 µm to 1000 µm. Typical thicknesses are in the ranges of 5 µm to 100 µm and preferably of 8 µm to 30 µm.

The anti-adhesive film or layer can be connected to the material of the basic structure over the full surface of the anti-adhesive film/layer or over part of the surface of the anti-adhesive film/layer, e.g. by laminating, welding, gluing and/or sewing (e.g., lamination of a bi-layer film comprising a MONOCRYL film and PDS film). Additional material used for laminating, gluing and/or sewing may be permanent (non-absorbable), absorbable or partially absorbable.

In another main aspect of the invention, the surgical implant provides to the surgeon clear indications to its location and orientation, even if the boundaries of the implant are concealed by bodily tissue. To this end, the center area of the mesh-like basic structure is marked by a center marking, and directional indicators point from the center marking to at least two corners of the outer periphery of the basic structure. Preferably, directional indicators point from the center marking to all of the corners of the outer periphery of the basic structure. The center marking can be a marking indicating a particular point like the center of gravity of the implant, e.g. a cross, but it can also be an extended marking arrangement which marks the central area of the implant in a different, but unambiguous way. Such center marking and directional indicators can also be used with mesh-like basic structures without pockets.

In advantageous embodiments of the invention, the directional indicators are provided as line marks (e.g., continuous lines or dashed lines, etc.) extending from the center marking up to the respective corner of the outer periphery of the basic structure, which tends to maximize the desired effect of a clear indication of the position and orientation of the implant during surgery.

The center marking and/or the directional indicators can be shaped from a film structure connected to the basic structure. They may also be formed from a threaded structure connected to the basic structure, e.g. embroidered on the basic structure or sewn on the basic structure. It is also conceivable that the center marking and/or the directional indicators are made in one piece with the basic structure; e.g. incorporated in a warp-knitting process. Preferably, the center marking and/or the directional indicators are dyed, but they could be undyed as well, provided there is a good contrast to the rest of the surgical implant. The center marking and/or the directional indicators can be made from absorbable or from non-absorbable materials.

Advantageous materials for the basic structure include, e.g., polypropylene, fluorinated polyolefines, blends of polyvinylidene fluoride and copolymers of vinylidene fluoride and hexafluoropropene (e.g. PRONOVA™ Poly(Hexafluoropropylene-VDF) material of Ethicon), which are all non-absorbable, or poly-p-dioxanone (PDS), copolymers of glycolide and lactide, copolymers of glycolide and lactide in the ratio 90:10 (e.g. VICRYL™ (polyglactin 910) synthetic absorbable filaments of Ethicon), copolymers of glycolide and ϵ-caprolactone (e.g. MONOCRYL absorbable material of Ethicon), which are all absorbable. Other biocompatible materials for the basic structure, as generally known in the art, are conceivable as well. Moreover, the basic structure can comprise a mixture of different materials, including a mixture or absorbable and of non-absorbable materials.

In advantageous embodiments, the basic structure is macroporous, e.g. having a pore size of at least 1 mm. Preferably, it is a light-weight construction having an areal weight of less than 50 g/m$^2$, but it could also be heavier. The basic structure can comprise, e.g., a warp-knit, a weft-knit, a crochet-knit, a woven fabric and/or a perforated film. If it includes filaments, the filaments may be bio-absorbable or non-absorbable, and the filaments can comprise monofilaments and/or multi-filaments (including multi-filaments made from different materials). Tape yarns and/or drawn film tapes are conceivable as well.

In summary, the surgical implant comprising pockets, in particular when designed as "Ventral Hernia Device" (VHD) with tissue-separating properties (anti-adhesive film), offers a plurality of advantages compared to the prior art. In contrast to the implants which are currently available on the market, repair layer and fixation layer (pocket) of the VHD can be formed by folding only one flexible blank. In this context, the fixation layer consists of several folded flaps which can overlap at the edges with the adjacent flaps. Fusing these preferably strip-like material doublings leads to palpable areas which are oriented to the corners of the implant. Therefore, the fused strips allow a better tactile control and guidance to the corners which lead to an improved intra-operative handling of the device. Furthermore, the pouch (pocket) formation out of only one flexible blank enables fixation at the outermost positions of the device edges and corners. Non-fixated edge areas with disadvantageous consequences are avoided. The VHD can be covered on the visceral side (repair layer) with an anti-adhesive, resorbable layer which extends to the parietal side (fixation layer). The covered edges provide additional protection regarding adhesion formation.

The folding of the surgical implant from one flexible blank also results in a significant material reduction and in an increased area available for tissue ingrowth, because seams along the periphery of the basic structure can be avoided. The stiffness of the fixation layer can be influenced by the shape of the overlap areas of the pockets and the kind of connection in the overlap areas.

Moreover, the repair layer may contain a marking guide (center marking and the directional indicators), which is linked to the outer shape of the implant and indicates the implant center and the position of the corners. This marking guide assists the surgeon in knowing the current position and orientation of the implant, enables a controlled fixation with evenly placed staples and offers the possibility for a standardized fixation approach during the surgery (first fixation points are predefined and can be found intuitively by following the marking guide).

A surgical implant comprising a center marking and directional indicators according to the invention can also be useful in designs without pockets.

BRIEF DESCRIPTION OF THE SEVERAL
VIEWS OF THE DRAWINGS

In the following, the invention is explained in more detail by means of embodiments. The drawings show in FIG. 1 in parts (a) to (d) several views of a first embodiment of the surgical implant according to the invention, i.e. in part (a) an explosion view of the components of the implant, in part (b) an isometric view of the partially finished implant, in part (c) a plan view of the implant and in part (d) an isometric view of the implant, FIG. 2 in parts (a) to (f) several views of a second embodiment of the surgical implant according to the invention, i.e. in part (a) an isometric view of a blank for the implant, in part (b) an explosion view of the blank and an anti-adhesive film, in part (c) a plan view of the blank with anti-adhesive film illustrating melt-glue areas, in part (d) an isometric view of the partially finished implant, in part (e) a plan view of the implant and in part (f) an isometric view of the implant, FIG. 3 in parts (a) to (e) several views of a third embodiment of the surgical implant according to the invention, i.e. in part (a) an isometric view of a blank for the implant, in part (b) an explosion view of the blank and an anti-adhesive film, in part (c) an isometric view of the partially finished implant, in part (d) a plan view of the implant and in part (e) an isometric view of the implant, FIG. 4 in parts (a) to (e) several views of a fourth embodiment of the surgical implant according to the invention, i.e. in part (a) an isometric view of a blank for the implant, in part (b) an explosion view of several layers used in the assemblage of the implant, in part (c) an isometric view of the partially finished implant, in part (d) a plan view of the implant and in part (e) an isometric view of the implant, FIG. 5 a schematic plan view of an illustrative embodiment of the surgical implant according to the invention which shows several designs for connecting the overlap areas between adjacent flaps, and FIG. 6 in parts (a) to (c) several schematic representations as examples for the arrangement of center markings and directional indicators in surgical implants according to the invention.

DETAILED DESCRIPTION OF THE
INVENTION

FIG. 1 illustrates a first embodiment of a surgical implant, which is designated by reference numeral 100, as well as a process of manufacturing the implant 100.

Figure 1A:
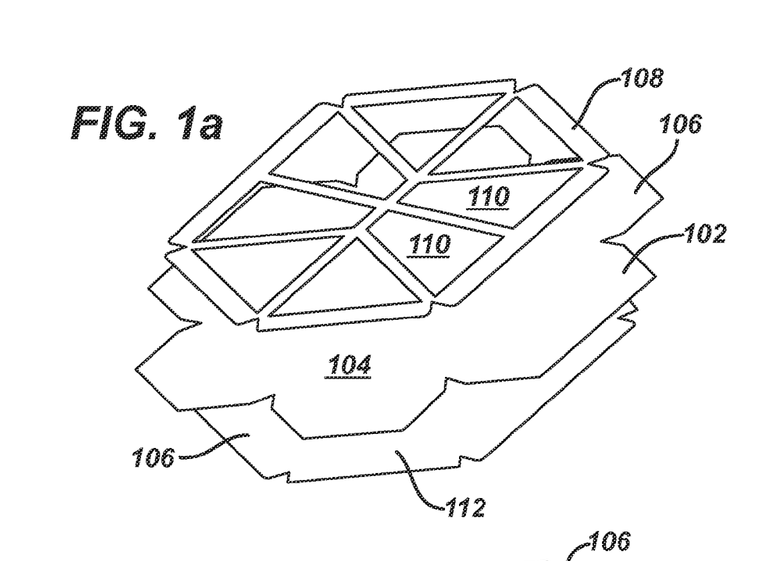

As shown in the explosion view of FIG. 1(a), the implant 100 is made of three parts. One part is a blank 102 consisting of a mesh-like material, in the embodiment a knitted, undyed monofilament polypropylene mesh (PROLENE™ Polypropylene Mesh of Ethicon; non-absorbable) comprising a filament thickness of 89 µm. The blank 102 defines a basic structure 104 of the implant 100 plus six flaps 106.

On top of the blank 102, FIG. 1(a) shows a marking layer 108 composed of a dyed (violet) film of poly-p-dioxanone (PDS) having a thickness of 50 µm (absorbable) and comprising a total of eight openings 110. The openings 110 can be punched or cut, e.g. by laser-cutting.

The third part visible in FIG. 1(a) is the blank of an anti-adhesive film 112. In the embodiment, the anti-adhesive film 112 is a MONOCRYL film (undyed) of 20 µm thickness. MONOCRYL material (Ethicon) is an absorbable copolymer of glycolide and ε-caprolactone and has anti-adhesive properties.

The three layers 102, 108 and 112 are placed on top of each other and laminated by heat. In that step, the poly-p-dioxanone of the layer 108 melts or gets very soft and penetrates through the pores of the blank 102 so that it well attaches to the blank 102 and additionally glues the anti-adhesive film 112 to the blank 102 so that part of the area of the anti-adhesive film 112 adheres to the blank 102.

Figure 1B:
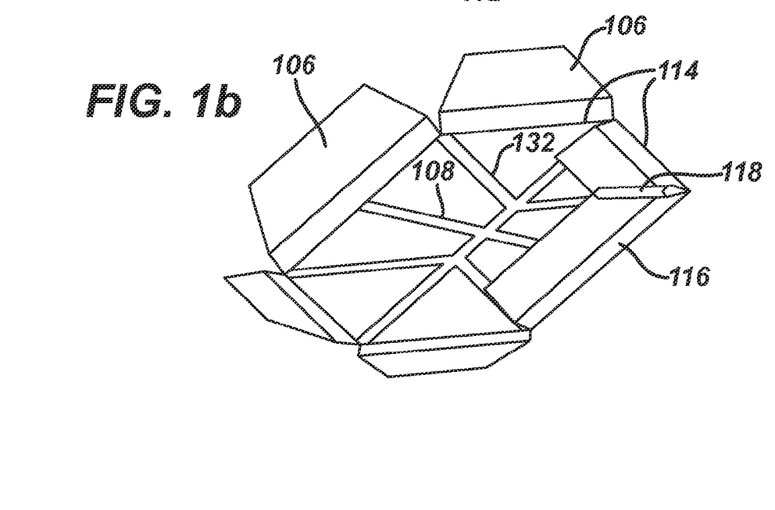

Afterwards, as shown in FIG. 1(b), the flaps 106 are folded about respective fold lines 114, which run through the edge areas of the anti-adhesive film 112 so that zones 116 of the anti-adhesive film 112 are formed which are folded as well but do not completely cover the flaps 106.

Adjacent flaps 106 overlap somewhat in their common edge zones, so that overlap areas 118 are provided. In the overlap areas 118, the material of adjacent flaps 106 is connected to each other, in the embodiment fused by ultrasonic welding in a strip-like shape.

Figure 1C:
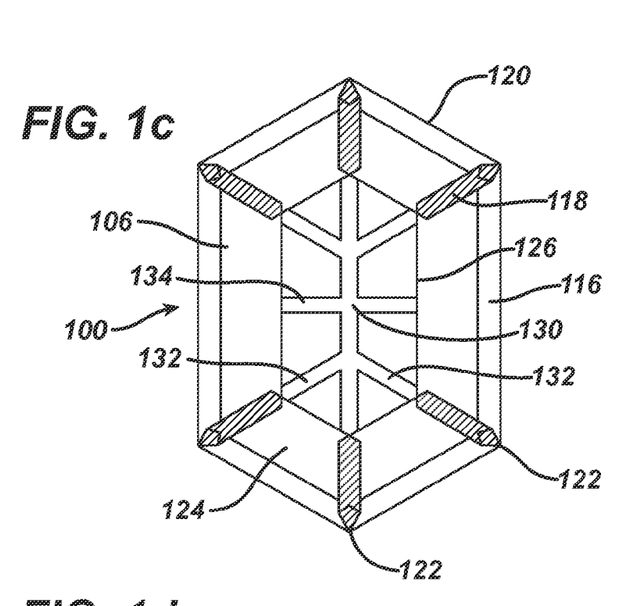

FIG. 1(c) illustrates the finished implant 100 in a top plan view. The fold lines 114 define an outer periphery 120 of the basic structure 104. In the embodiment, the basic structure 104, i.e. the finished implant 100, has a hexagonal shape including six corners 122. Six pockets 124 are formed by the flaps 106 and the opposing material of the basic structure 104. These pockets are accessible via edges 126 defined by part of the outer edge of the original blank 102.

The marking layer 108 provides a center marking 130, six directional indicators 132 pointing to and extending up to the corners 122, and additionally a middle line indicator 134 which also extends up to the outer periphery 120 of the implant 100. In FIG. 1(c), the overlap areas 118 are hatched, but since the mesh material of the blank 102 is translucent, the directional indicators 132 and also the middle line indicator 134 are well visible through the flaps 106 when the implant 100 is viewed from its top side displayed in FIG. 1(c).

Figure 1D:
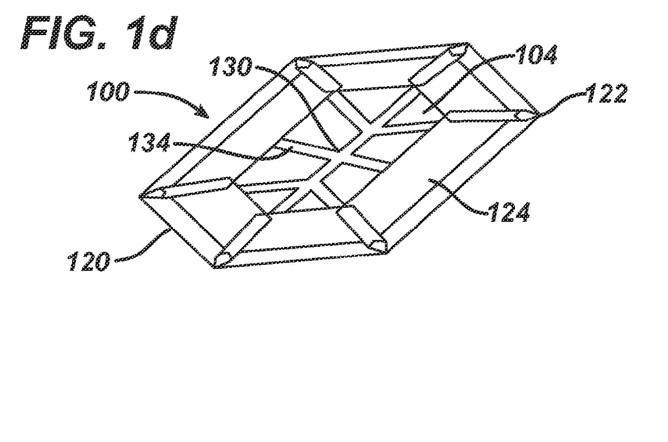

FIG. 1(d) is an isometric view of the implant 100 from the top.

The surgical implant 100 is flexible and comprises a mesh-like areal structure. The center marking 130 and the directional indicators 132 permit a certain assessment of the position and orientation of the implant 100, even if its outer periphery 120 is not or not completely visible. In the overlap areas 118, the material has double thickness, which provides a tactile response, thus facilitating the surgical procedure. Moreover, the hexagonal shape of the implant 100 with six well-defined corners 122 (which nevertheless could be somewhat rounded in an atraumatic manner) additionally improves the handling properties of the implant 100.

Since material of the marking layer 108 is also present in the area of the fold lines 114, the outer periphery 120 of the implant 100 is also well visible (unless hidden by bodily tissue).

Preferably, the implant 100 is attached to bodily tissue by introducing a stapling instrument into the pockets 124 and expelling the staples so that they penetrate just the flaps 106, pointing away form the basic structure 104. This procedure can be performed in a well-defined way, e.g. one staple can be placed in the area of each corner 122 so that it penetrates the material of the flaps 106 in the overlap areas 118, which are stronger because of double-thickness.

Figures 2A, 2B, 2D, 2E, 2F:
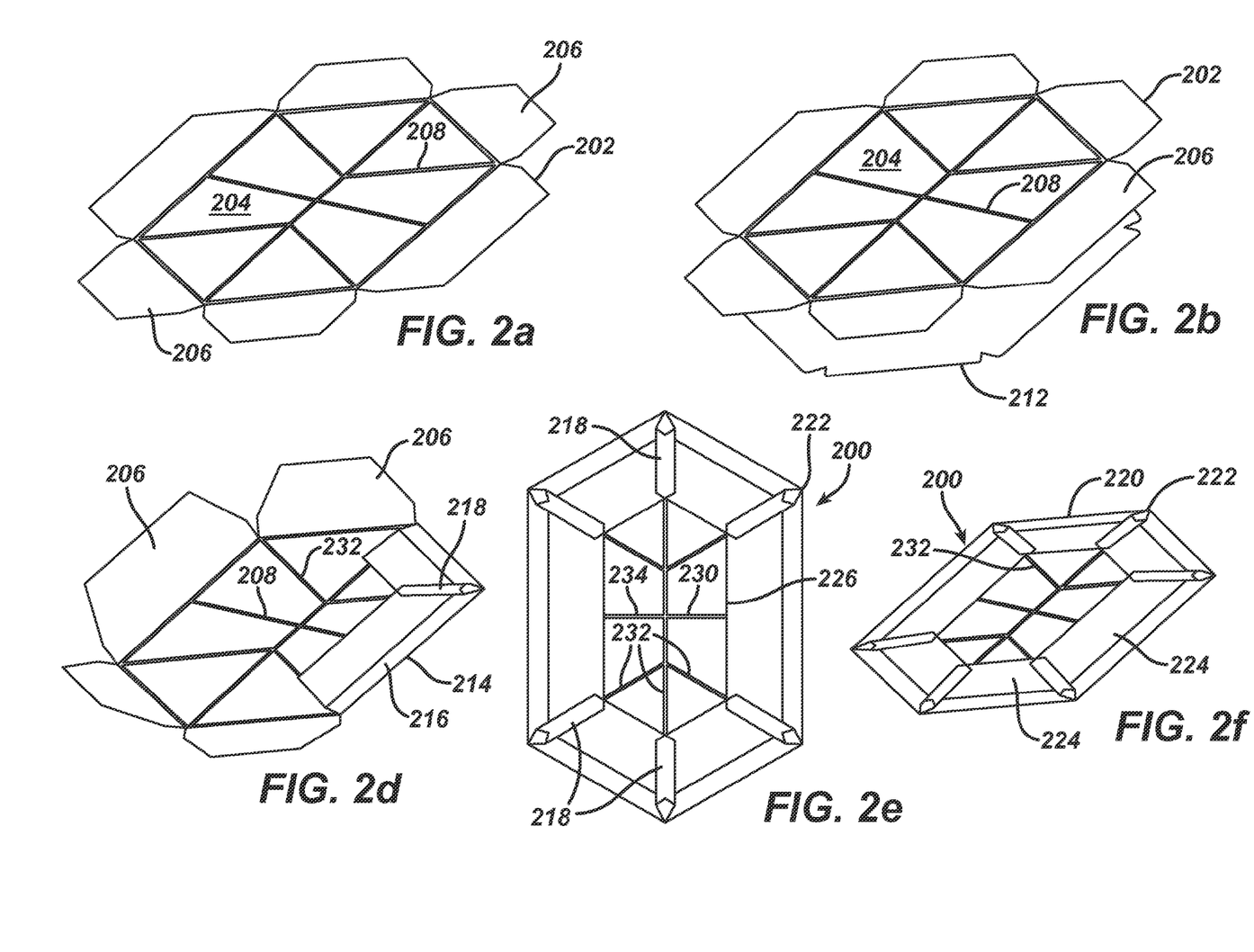
Figure 2C:
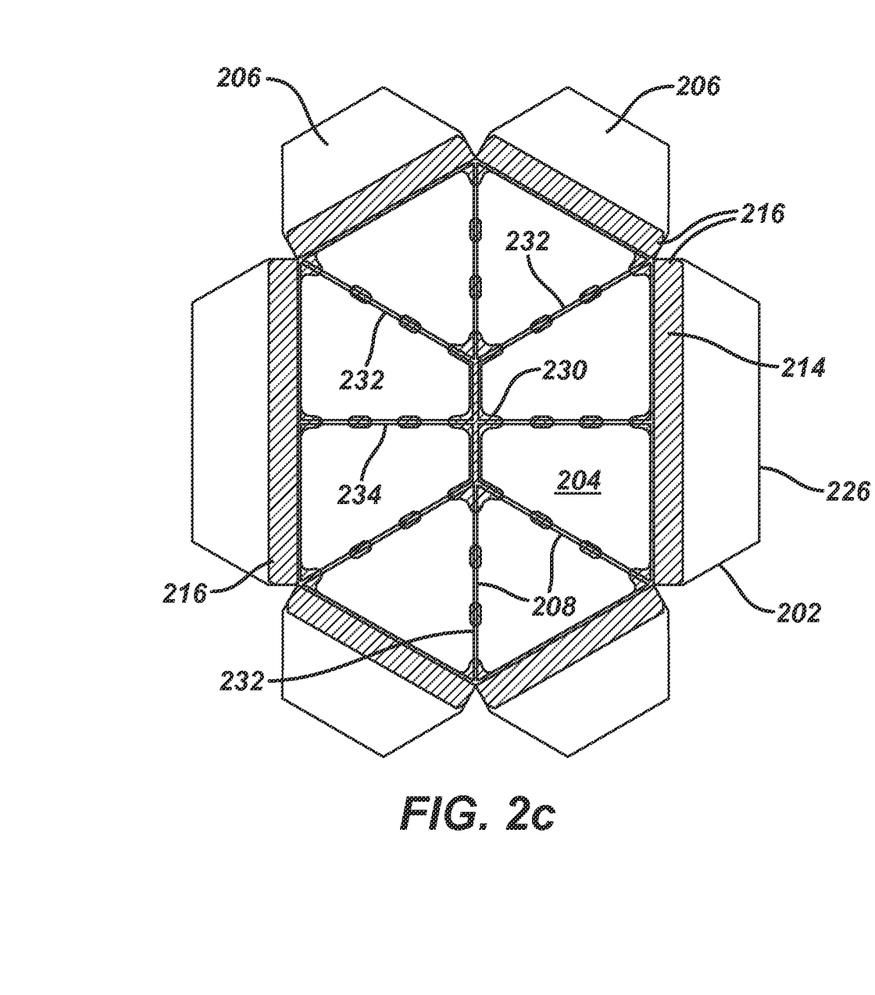

A second embodiment of the surgical implant, designated by reference numeral 200, is illustrated in FIG. 2. The implant 200 is similar to implant 100. For that reason, the parts and components of the implant 200 are not explained again in detail. In the following, only the differences between the implants 100 and 200 are pointed out. In FIG. 2, the respective associated reference numerals from FIG. 1 have been increased by 100.

Blank 202 is cut from a knitted partially absorbable mesh material made from undyed monofilaments of polypropylene (89 μm thick; PROLENE Polypropylene) and dyed (violet) monofilaments of poly-p-dioxanone (81 μm thick; PDS).

In implant 200, a center marking 230 and directional indicators 232 are not provided via a film-like marking layer, but by threads 208 of absorbable violet poly-p-dioxanone monofilaments (109 μm thick; PDS), which are sewn to blank 202 in order to form the center marking 230, six directional indicators 232, a middle line indicator 234 as well as a hexagonal line along the outer periphery 220 of the implant 200, see FIG. 2(a).

The flexible blank 202 and an anti-adhesive, absorbable layer 212 (see FIG. 2(b)), in the embodiment a 20 μm thick undyed Monocryl film, are connected partially in the area of the sewn marking threads 208 of PDS and in zones 216, see FIG. 2(c). To this end, the assembly is heated in pre-selected areas (hatched in FIG. 2(c)) so that the PDS material of the blank 202 and the marking threads 208 melts in these areas and acts as a melt-glue, similar to the first embodiment. In overlap areas 218, the folded flaps 206 are fused by ultrasonic welding in a strip-like shape, see FIG. 2(d). FIGS. 2(e) and 2(f) display the finished implant 200.

Figures 3A, 3B, 3C, 3D, 3E:
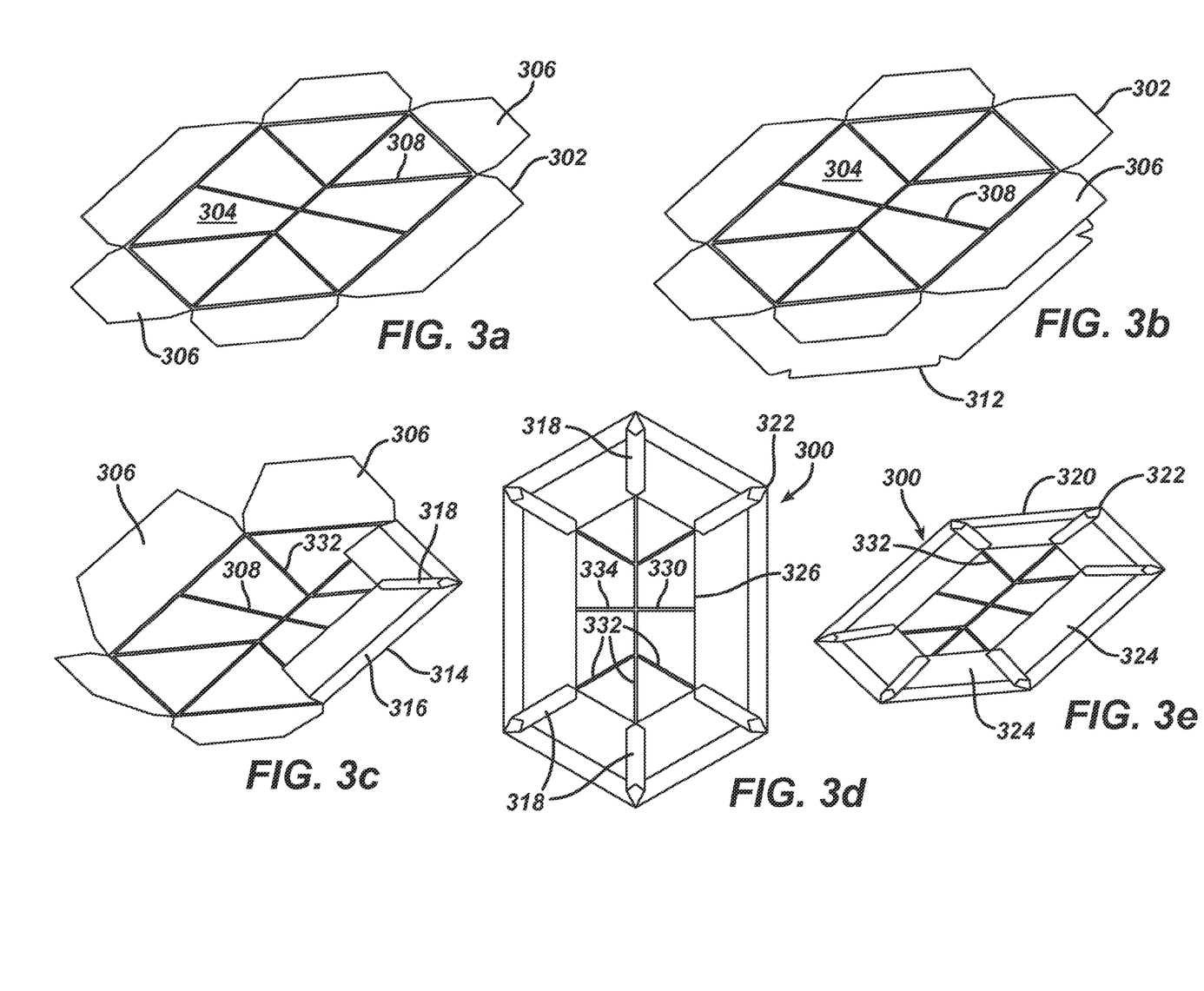

A third embodiment of the surgical implant, designated by reference numeral 300, is illustrated in FIG. 3. The implant 300 is similar to implant 200. Again, the respective associated reference numerals have been increased by 100. In implant 300, the material for blank 302 and sewn marking threads 308, respectively, is the same as in implant 200.

In contrast to implant 200, anti-adhesive film 312 (again of undyed MONOCRYL film) is only 10 μm thick and is connected across its entire surface to blank 302. To achieve the latter, during the lamination process the heat is controlled to sufficiently soften or melt the PDS filaments in the blank 302 opposing the anti-adhesive film 312 and not just in the marking threads 308. In the overlap areas 318, the folded flaps 306 are fused by ultrasonic welding in a strip-like shape, as in the other embodiments.

FIG. 3(a) shows the blank 302 with the marking threads 308, FIG. 3(b) additionally the anti-adhesive film 312, FIG. 3(c) the partially finished implant 300, and FIGS. 3(d) and 3(e) show the finished implant 300.

Figures 4A, 4B, 4C, 4D, 4E:
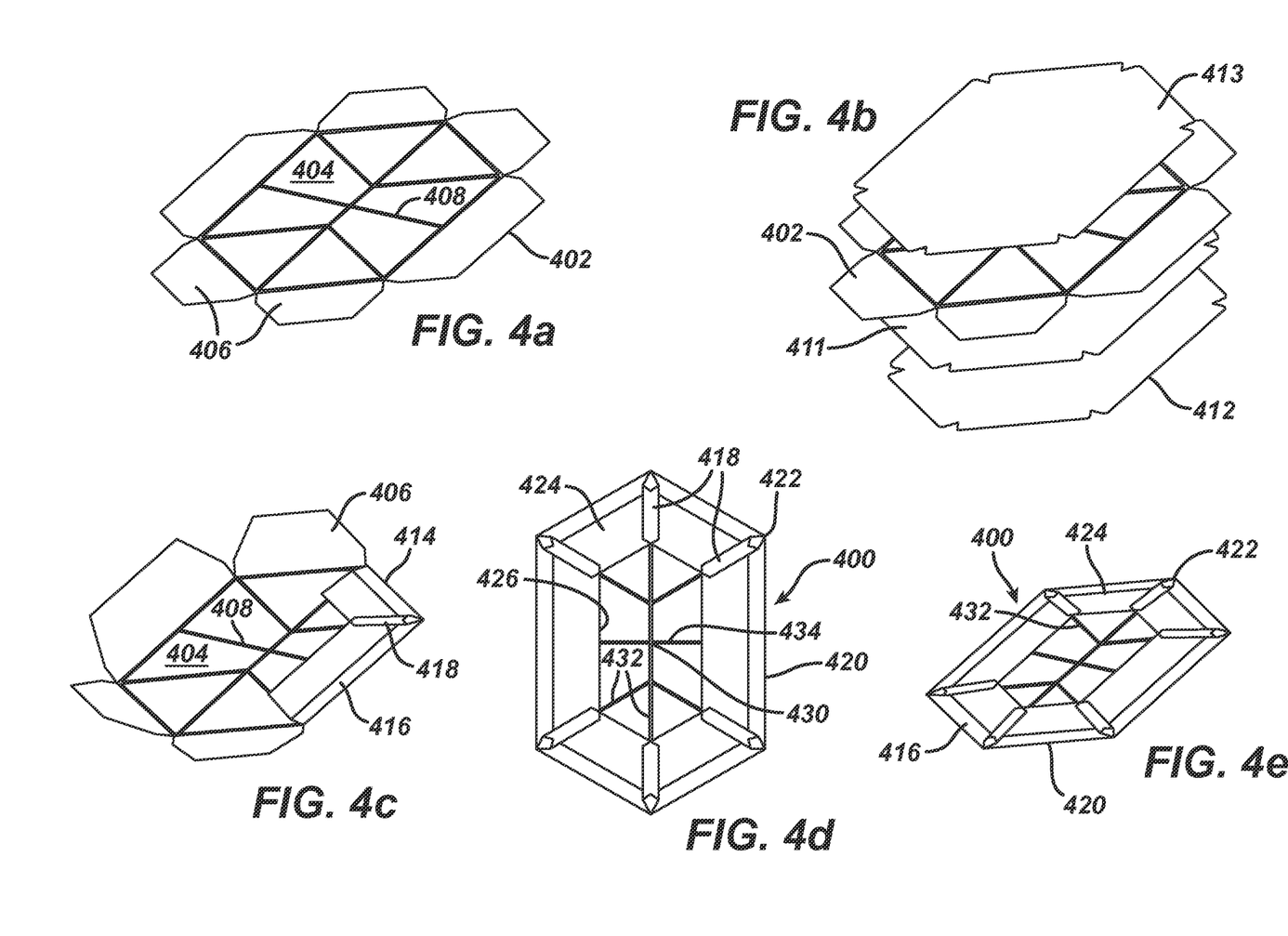

FIG. 4 illustrates a fourth embodiment of the surgical implant, designated by reference numeral 400. Because of the similarity to the other embodiments, the respective associated reference numerals again have been increased by 100.

Blank 402 is made from a knitted mesh of 89 μm thick polypropylene monofilaments (PROLENE Polypropylene; dyed and undyed), which includes in the central area a marking guide 408 sewn with dyed polypropylene monofilaments (89 μm thick; PROLENE Polypropylene), see FIG. 4(a).

The flexible blank 402 and an anti-adhesive, resorbable layer 412 of oxidized regenerated cellulose (ORC; undyed) are connected by using an intermediate layer 411 made of an undyed PDS film of 20 μm thickness and an additional layer 413 made of an undyed, absorbable PDS film of 5 μm thickness as a hot-melt adhesive, see FIG. 4(b). In the overlap areas 418, the folded flaps 406 are fused by ultrasonic welding in a strip-like shape, as in the other embodiments. FIG. 4(c) shows the partially finished implant 400, and FIGS. 4(d) and 4(e) show the finished implant 400.

Figure 5:
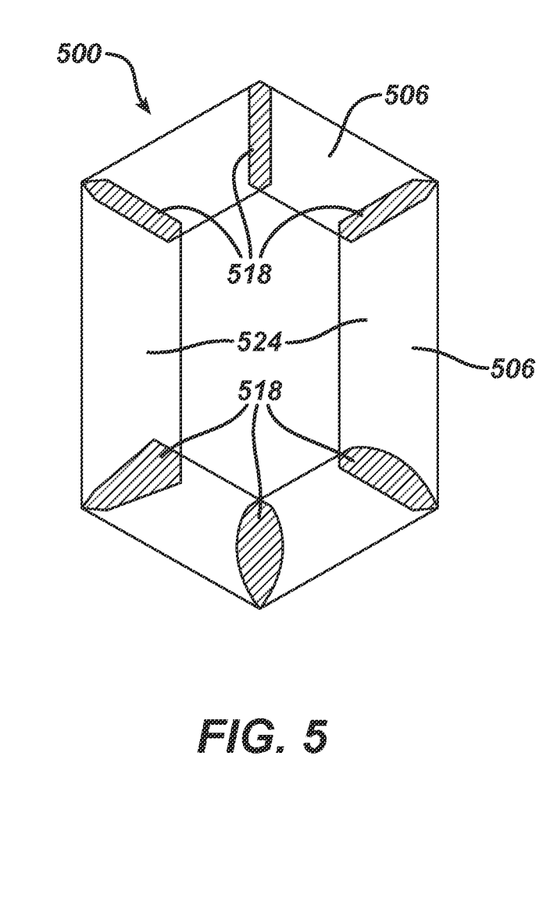

FIG. 5 illustrates various shapes of overlap areas 518 (hatched), in which adjacent flaps 506 of a surgical implant 500 are connected to each other. By designing the size and shape of the overlap areas 518, the properties of pockets 524 (in particular in terms of flexibility) can be influenced. Usually, the shape will be the same for all overlap areas in a given implant, like in the surgical implants 100, 200, 300 and 400, but assemblies like that in FIG. 5 are conceivable as well, in particular when symmetric with respect to axes of symmetry.

In different embodiments of the surgical implant, adjacent flaps are not connected in the overlap areas or do not overlap at all.

Figure 6A:
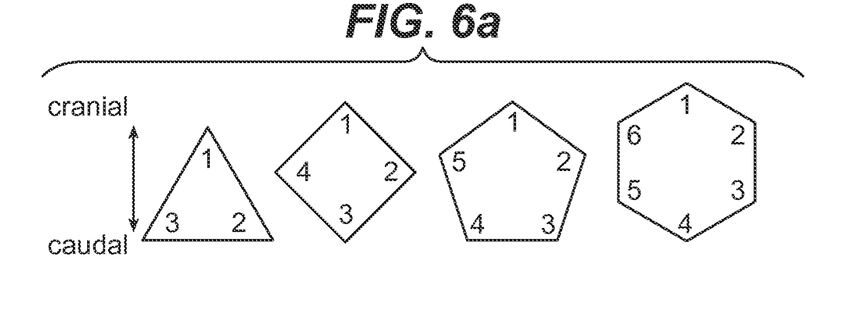
Figure 6B:
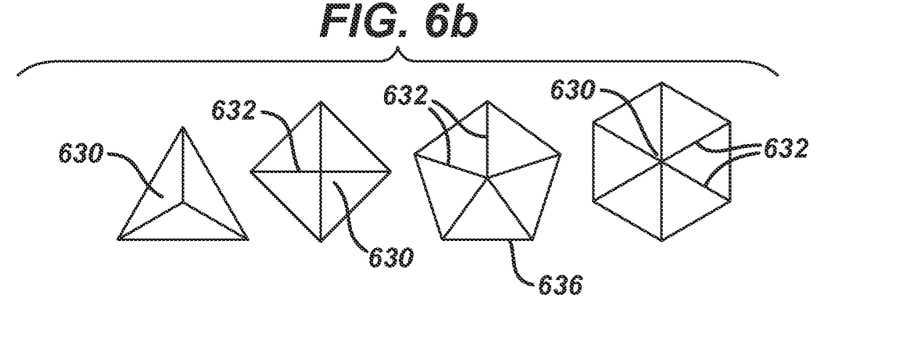
Figure 6C:
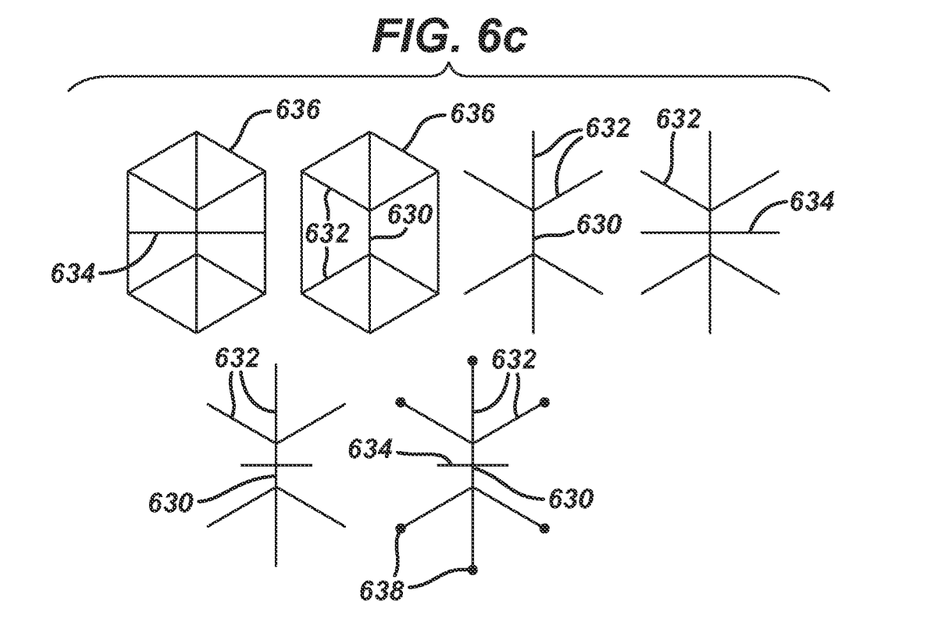

FIG. 6 displays some schematic representations of basic structure shapes and center markings and directional indicators for embodiments of the surgical implant.

In FIG. 6(a), a preferred orientation of polygonal implants with three to six corners with respect to the anatomical environment is indicated.

FIG. 6(b) shows examples of equilateral polygons, in which the center marking 630 is point-like and indicates the center of gravity of the respective implant. The directional indicators 632 extend up to the corners of the implant. Additional marking lines 636 are provided along the periphery of the implant.

The implants in the examples of FIG. 6(c) have a hexagonal shape like the implants 100, 200, 300 and 400. In two cases, marking lines 636 are included along the periphery of the implant. In the other cases, there are no such marking lines. In all cases, the directional indicators 632 extend up to the corners. In one case, the corners are additionally marked by extended dots 638. However, the directional indicators will be helpful even if they do not reach the corners. In some cases, additional midline indicators 634 are provided. It is evident from FIG. 1(c) that the center area of each implant is easily assessable, even if a center marking 630 is not point-like. Many other examples for the arrangement of the marking lines are conceivable as well.

The embodiments described above illustrate the general concept of the surgical implant according to the invention, when designed as a Ventral Hernia Device (VHD) in preferred variants. In summary:

The Ventral Hernia Device (VHD) is a pocket-shaped device with tissue-separating properties for the reinforcement and bridging of the abdominal wall in ventral, incisional and larger umbilical hernia repair, using an open intra-peritoneal onlay mesh technique.

VHD comprises a polygonal flexible basic structure with a central area (repair layer) and peripheral flaps (fixation layer). The flaps form pockets, but do not extend up to the geometric center of the fixation layer so that the fixation layer has a central opening and the pockets form a kind of pouch which is easily accessible via this central opening. Flap folding and fusion at overlap areas leads to a preferably strip-like doubling of the fixation layer in such a manner that the strips are oriented to the corners; the areas of doubling may cover between 1% and 50% of the fixation layer area, preferably 1% to 20%. The fused strips allow for a better tactile control and guidance to the corners, which leads to an improved intra-operative handling of the implant.

The central opening in the fixation layer enables entry of a finger or surgical instrument such as a stapler into the space created between the visceral and parietal side, i.e. into the pockets. The pocket formation by folding of only one flexible blank enables a fixation at the outermost position of the periphery and corners of the implant, which results in a flatly spread out implant. Non-fixated edge material (as in the case of products with supporting rings or seams to connect different layers) is avoided so that bulging or folding of non-fixated edge material usually does not occur.

On the visceral side (repair layer), the implant is covered with an anti-adhesive, absorbable layer, which is fixated on the basic structure from one side and also covers the edges at the periphery of the implant where it extends from the visceral side to the parietal side, which leads to a partially covered fixation layer. Preferably, less than 50% of the fixation layer is covered with the absorbable layer, which allows very good tissue ingrowths. Moreover, such an extended absorbable layer provides additional edge protection regarding adhesion formation.

The surgical implant having mesh pockets can be used in the so-called open-IPOM technique for the repair of ventral hernias. For the fixation of the mesh pockets, it has been found that it is advantageous to start the fixation of the mesh pockets in the axis of cranial/caudal, then to fix the other vertices, and then to complete the fixation according to the usual known techniques. In this procedure, starting with the fixation in the axis of cranial/caudal, it was observed that the tendency for forming folds in the implant, which is caused by uneven fixation of the mesh pockets on the relatively soft abdominal wall, is clearly reduced, and the implants are integrated significantly better (tissue ingrowths) in the abdominal wall.

A marking guide (center marking and directional indicators) at the repair layer, which is linked to the outer shape of the implant and indicates the implant center and the position of the corners, helps the surgeon to know the actual device position and orientation without additional lifting of bodily tissue or implant manipulation and enables a controlled fixation with evenly placed staples or clips. This also offers to the surgeon the possibility for a standardized fixation approach (e.g., the initial fixation points are predefined and can be found intuitively by following the marking guide). The shape of the mesh pockets and a better visualization of the mesh edges/corners improve the intra-operative handling to a considerable extent.

The marking guide (center marking and directional indicators) is also very useful in areal surgical implants (in particular mesh-like structures) without pockets.

Generally, the outer contour or shape of implant meshes according to the prior art does not provide reference to the surgeon to consider direction-dependent properties of the repair mesh, such as achieving a certain coverage or overlap of the defect, the stretch properties of the mesh, the orientation during fixation, a guide to the first fixation points, or a clear identification of the area where to fixate. On the other hand, a correct placement in terms of orientation and centering of the implant over the defect is crucial for a successful repair. And wrinkling and folding of the implant during fixation lead to wrinkle cavities (and in consequence to seroma formation), which results in a poor integration of the implant into the abdominal wall.

Such problems can be avoided when the mesh-like basic structure of the implant has a polygonal shape and when the implant comprises a marking guide, i.e. a center marking and directional indicators pointing from the center marking to the corners. The link between shape and marking guide helps the surgeon to know the current position and orientation of the implant just by looking in the center of the defect without additional lifting of the tissue or implant manipulation. The implant can be positioned in a better way, compared to prior art, for example when a corner tip of the implant is put under osseous structures like the sternum.

Starting the fixation in the vertices (corner areas) of the implant by following the continuous marking guide with the fixation device from the implant center to the vertices leads to a flat spreading of the implant with evenly placed staples. This offers to the surgeon the possibility for a structured and standardized fixation approach, e.g. in that the first fixation points are predefined and can be found intuitively following the marking guide. A hexagonal shape of the implant is particularly advantageous.

For example, during implantation for repair of an incisional hernia with a tetragonal mesh (square or rectangular), a marking guide pointing to the vertices or corners "1" and "3", as shown in FIG. 6(a), can indicate the cranial-caudal direction. For a hexagonal shape, the corners "1" and "4" indicate the cranial-caudal direction. The cranial-to-caudal orientation can be displayed in a pentagonal mesh shape through the corner point "1" and the center of the basis between corner points 3 and 4.

The invention claimed is:

1. A surgical implant for repairing a tissue or muscle wall defect, comprising a mesh-like, flexible basic structure having a flat base member, a top side, a bottom side, a center area and an outer periphery, characterized in that the outer periphery comprises a polygonal shape having N corners, wherein N is at least 3;

a plurality of flap members extending from the outer periphery of the base member and each flap connected to the periphery by a fold line, the flap members having opposed side edges, a free lateral edge, and a top and a bottom;

wherein the flap members are folded upwardly about the fold lines such that the side edges overlap to form an accessible pocket between the top of base member and the bottom of the flap members wherein the sides edges overlap to form an overlap area, and wherein adjacent flaps are fused to each other in the overlap area;

a center marking on the top side of the base member; and, an anti-adhesion barrier film on the bottom side of the base member.

2. A surgical implant according to claim 1, characterized in that N is selected from the following set: {6, 8}.

3. A surgical implant according to claim 1, characterized in that at least one of the overlap areas has one of the following shapes selected from the group consisting of: strip-like, curved, zigzag-shaped, asymmetric, and diamond-shaped.

4. A surgical implant according to claim 1, characterized in that in each overlap area, the adjacent flaps are fused by welding.

5. A surgical implant according to claim 1, characterized in that the anti-adhesion film covers the bottom side of the basic structure and extends beyond the outer periphery of the basic structure where the anti-adhesive film that extends beyond the outer periphery is folded back together with the flaps.

6. A surgical implant according to claim 1, characterized in that the anti-adhesion film is absorbable and comprises at least one of the substances selected from the group consisting of: poly-p-dioxanone, ε-caprolactone, copolymer of glycolide and ε-caprolactone, oxygenized re-generated cellulose, collagen, and combinations thereof.

7. A surgical implant according to claim 1, characterized in that the anti-adhesion film has a thickness in one of the following ranges selected from the group consisting of: 2 μm to 1000 μm, 5 μm to 100 μm, and 8 μm to 30 μm.

8. A surgical implant according to claim 1, characterized in that the anti-adhesion film is connected to the material of the bottom side of the basic structure in at least one of the following manners selected from the group consisting of: attachment over the full surface of the anti-adhesive film, attachment over part of the surface of the anti-adhesive film, laminated, welded, glued, sewed, permanent, absorbable, and partially absorbable.

9. A surgical implant according to claim 1, characterized in that the basic structure comprises at least one of the materials selected from the group consisting of polypropylene, fluorinated polyolefins, poly-p-dioxanone, copolymers of glycolide and lac-tide, copolymers of glycolide and lactide in the ratio 90:10, copolymers of glycolide and ε-caprolactone, and blends of polyvinylidene fluoride and copolymers of vinylidene fluoride and hexa¬ fluoropropene.

10. A surgical implant according to claim 1, characterized in that the basic structure comprises at least one of the properties selected from the group consisting of being macro-porous, having a pore size of at least 1 mm, having an areal weight of less than 50 g/m2, comprising a warp-knit, comprising a weft-knit, comprising a crochet-knit, comprising a woven fabric, comprising a perforated film, comprising bio-absorbable filaments, comprising non-absorbable filaments, comprising mono-filaments, comprising multi-filaments, comprising tape yarns, and comprising drawn film tapes.

11. A surgical implant according to claim 1, characterized in that the center marking is located in the center area of the mesh-like basic structure, wherein directional indicators point from the center marking to at least two corners of the outer periphery of the basic structure.

12. A surgical implant according to claim 11, characterized in that directional indicators point from the center marking to all of the corners of the outer periphery of the basic structure.

13. A surgical implant according to claim 11, characterized in that at least part of the directional indicators are provided as line marks extending from the center marking up to the respective corner of the outer periphery of the basic structure.

14. A surgical implant according to claim 11, characterized in that at least one of the center marking and the directional indicators comprises at least one of the properties selected from the group consisting of, shaped from a film structure connected to the basic structure, formed from a threaded structure connected to the basic structure, embroidered on the basic structure, sewn on the basic structure, made in one piece with the basic structure, dyed, undyed, absorbable, and non-absorbable.

* * * * *